(12) United States Patent
Hibner

(10) Patent No.: US 12,708,397 B2
(45) Date of Patent: Aug. 18, 2026

(54) REPLACEABLE SURGICAL SCISSOR BLADES FOR SURGICAL INSTRUMENTS

(71) Applicant: Cilag GmbH International, Zug (CH)

(72) Inventor: John A. Hibner, Mason, OH (US)

(73) Assignee: Cilag GmbH International, Zug (CH)

( * ) Notice: Subject to any disclaimer, the term of this patent is extended or adjusted under 35 U.S.C. 154(b) by 152 days.

(21) Appl. No.: 18/408,196

(22) Filed: Jan. 9, 2024

(65) Prior Publication Data

US 2025/0221730 A1 Jul. 10, 2025

(51) Int. Cl.

| | |
|---|---|
| ***A61B 17/32*** | (2006.01) |
| ***A61B 17/00*** | (2006.01) |
| ***A61B 17/3201*** | (2006.01) |
| ***A61B 90/00*** | (2016.01) |

(52) U.S. Cl.

CPC .... *A61B 17/3201* (2013.01); *A61B 17/00234* (2013.01); *A61B 90/08* (2016.02); *A61B 2017/00982* (2013.01)

(58) Field of Classification Search

CPC .......... A61B 17/3201; A61B 17/00234; A61B 90/08; A61B 2017/00982; A61B 2017/00477

See application file for complete search history.

(56) References Cited

U.S. PATENT DOCUMENTS

| | | | | |
|---|---|---|---|---|
| 2013/0158542 A1* | 6/2013 | Manzo | A61B 34/37 | 606/34 |
| 2023/0181207 A1* | 6/2023 | Kingsley | A61B 34/30 | 606/167 |
| 2024/0277370 A1* | 8/2024 | Lazzari | A61B 34/37 | |

* cited by examiner

*Primary Examiner* — Brooke Labranche

(74) *Attorney, Agent, or Firm* — Vorys, Sater, Seymour and Pease LLP

(57) ABSTRACT

A surgical tool includes a drive housing, an elongate shaft extending distally from the drive housing, a wrist arranged at a distal end of the shaft and including a distal clevis with first and second distally-extending arms, and an end effector operatively coupled to the wrist. The end effector including a first blade holder rotatably mounted to the first arm at a first axle, a second blade holder rotatably mounted to the second arm at a second axle, a first blade releasably coupled to the first blade holder with a first securing device, and a second blade rotatably coupled to the first blade at a center pin and releasably coupled to the second blade holder with a second securing device. Disengaging the first and second securing devices from the first and second blade holders allows the first and second blades to be separated from the first and second blade holders.

17 Claims, 9 Drawing Sheets

REPLACEABLE SURGICAL SCISSOR BLADES FOR SURGICAL INSTRUMENTS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some end effectors include high-wear components that can mechanically or physically degrade over time and thereby limit the useful life of the end effector. One example of high-wear components is the blades of surgical scissors, which can dull over time, and thereby adversely affect the efficiency of the end effector. What is needed is a method and system of more easily replacing the blades of an end effector, which can provide a user (e.g., a surgeon, a nurse, etc.) with a new set of blades for every new use of the surgical tool.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to methods and systems of replacing blades of end effector surgical scissors.

The embodiments disclosed herein describe a surgical tool that includes a drive housing, an elongate shaft extending distally from the drive housing, a wrist arranged at a distal end of the shaft and including a distal clevis with first and second distally-extending arms, and an end effector operatively coupled to the wrist. The end effector may include a first blade holder rotatably mounted to the first arm at a first axle, a second blade holder rotatably mounted to the second arm at a second axle, a first blade releasably coupled to the first blade holder with a first securing device, and a second blade rotatably coupled to the first blade at a center pin and releasably coupled to the second blade holder with a second securing device. Disengaging the first and second securing devices from the first and second blade holders allows the first and second blades to be separated from the first and second blade holders.

Embodiments described herein further disclose the use of disassembly and assembly cassettes to remove used blades from an end effector and reattach new blades to the end effector, thereby extending the useful life of the end effector.

Figure 1:
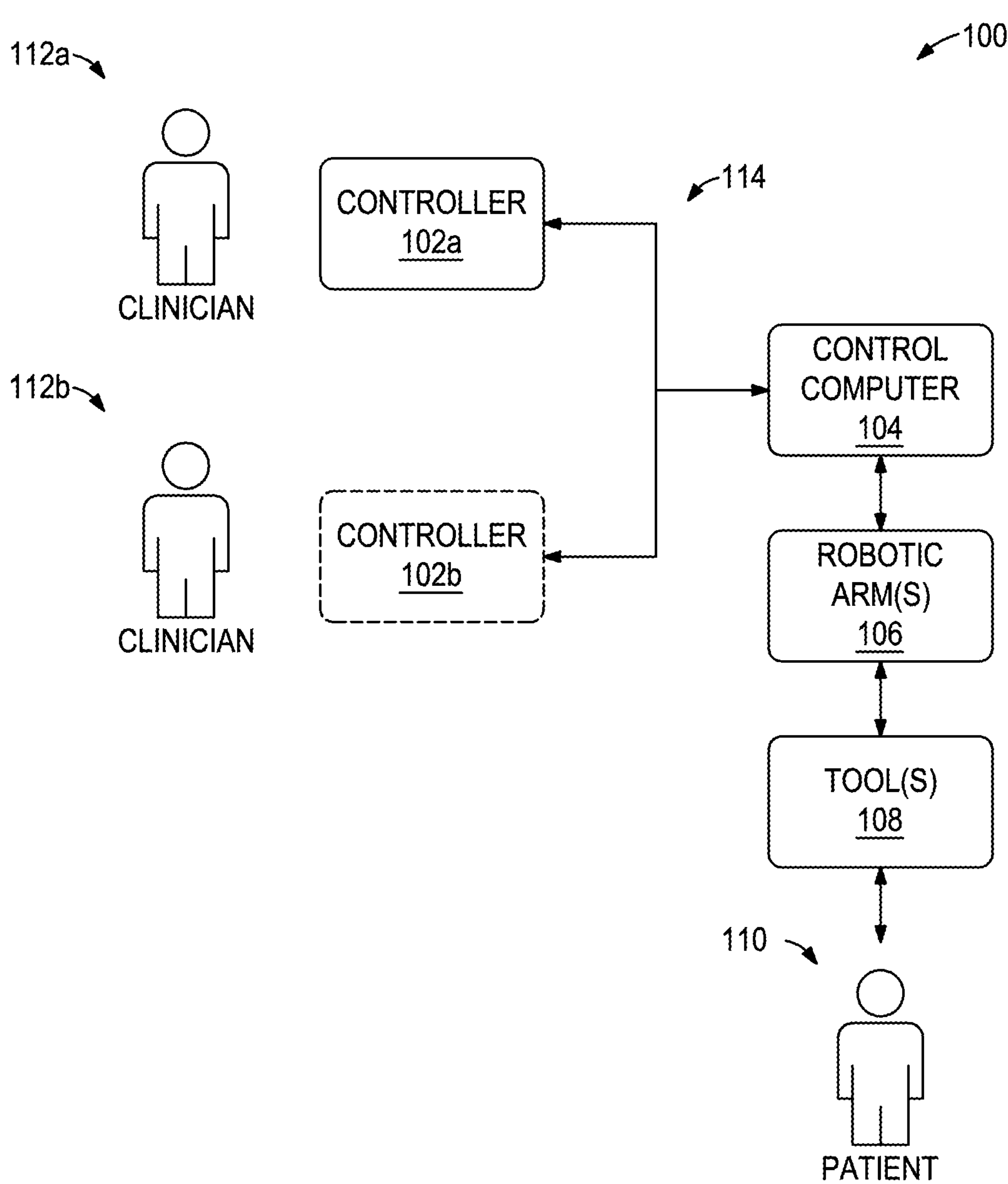
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
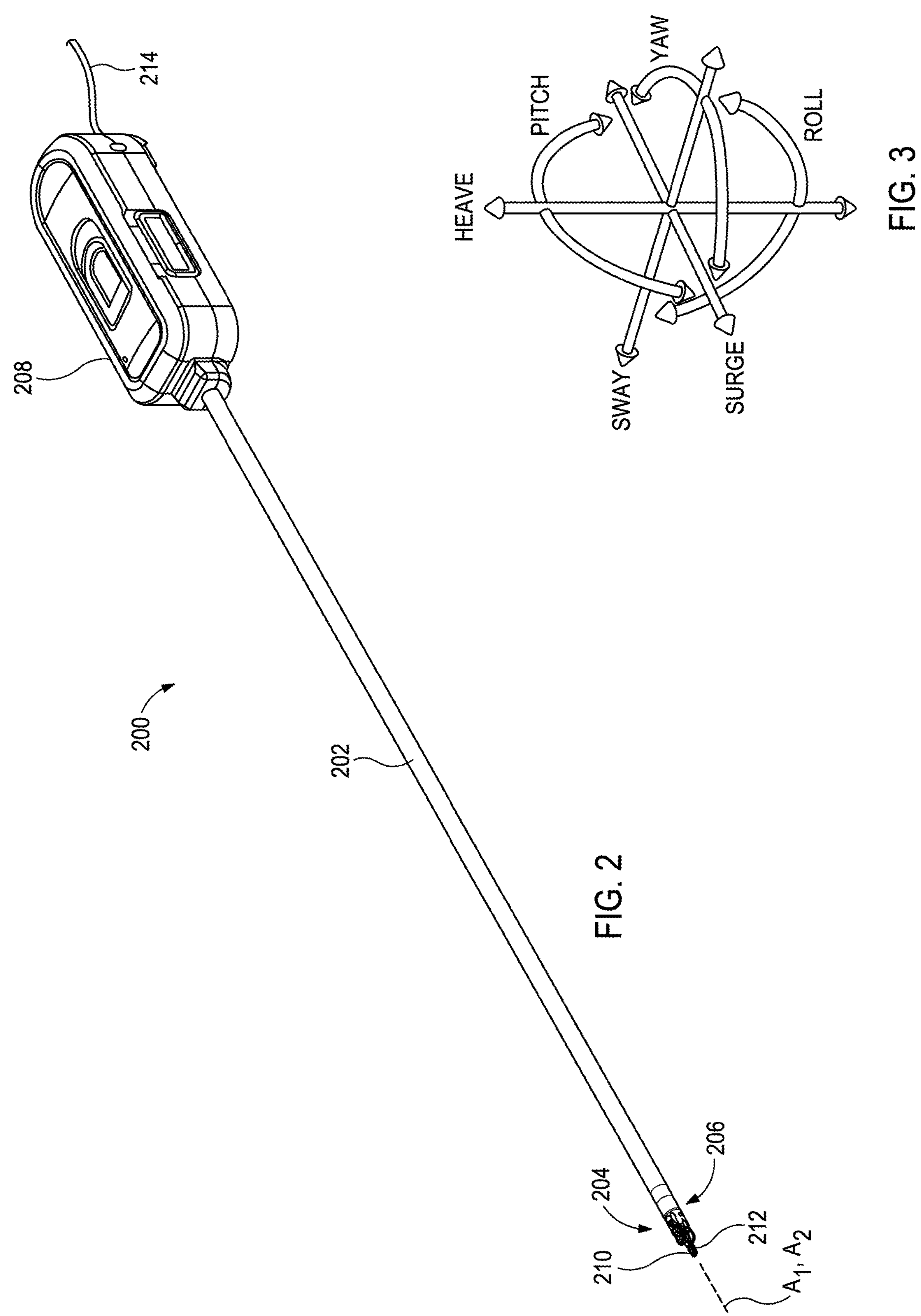
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises surgical scissors that includes opposing first (upper) and second (lower) blades 210, 212 configured to move (articulate) between open and closed positions. As will be appreciated, however, the blades 210, 212 may alternatively comprise opposing jaws that form part of other types of end effectors such as, but not limited to, a needle driver, a clip applier, a tissue grasper, a vessel sealer, a combination tissue grasper and vessel sealer, a babcock including a pair of opposed grasping jaws, bipolar jaws (e.g., bipolar Maryland grasper, forceps, a fenestrated grasper, etc.), etc. One or both of the blades 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator that supplies energy, such as electrical energy (e.g., radio frequency energy), ultrasonic energy, microwave energy, heat energy, or any combination thereof, to the surgical tool 200 and, more particularly, to the end effector 204. Accordingly, the generator may comprise a radio frequency (RF) source, an ultrasonic source, a direct current source, and/or any other suitable type of electrical energy source that may be activated independently or simultaneously.

Similar to most surgical tools, the surgical tool 200 includes various high-wear components (e.g., "consumables") that, over time, can mechanically or physically degrade and thereby limit the useful life of the surgical tool 200. For example, the blades 210, 212 are highly-utilized during many surgical procedures, and the cutting edges of the blades 210, 212 will inevitably dull over time, which can affect the proficiency of the end effector 204. Moreover, in embodiments where the blades 210, 212 are electrified (e.g., monopolar blades), the cutting edge of the blades 210, 212 may further degrade due to monopolar energy employed during procedures. Consequently, the end effector 204 may be designed to be used for only a predetermined number of procedures, and once reaching the predetermined number of procedures, the operator (e.g., a nurse, a doctor, etc.) may be unable to continue using the end effector 204. According to embodiments of the present disclosure, the blades 210, 212 can be easily and quickly replaced, thereby extending the useful life of the end effector 204 and the surgical tool 200.

Figure 4:
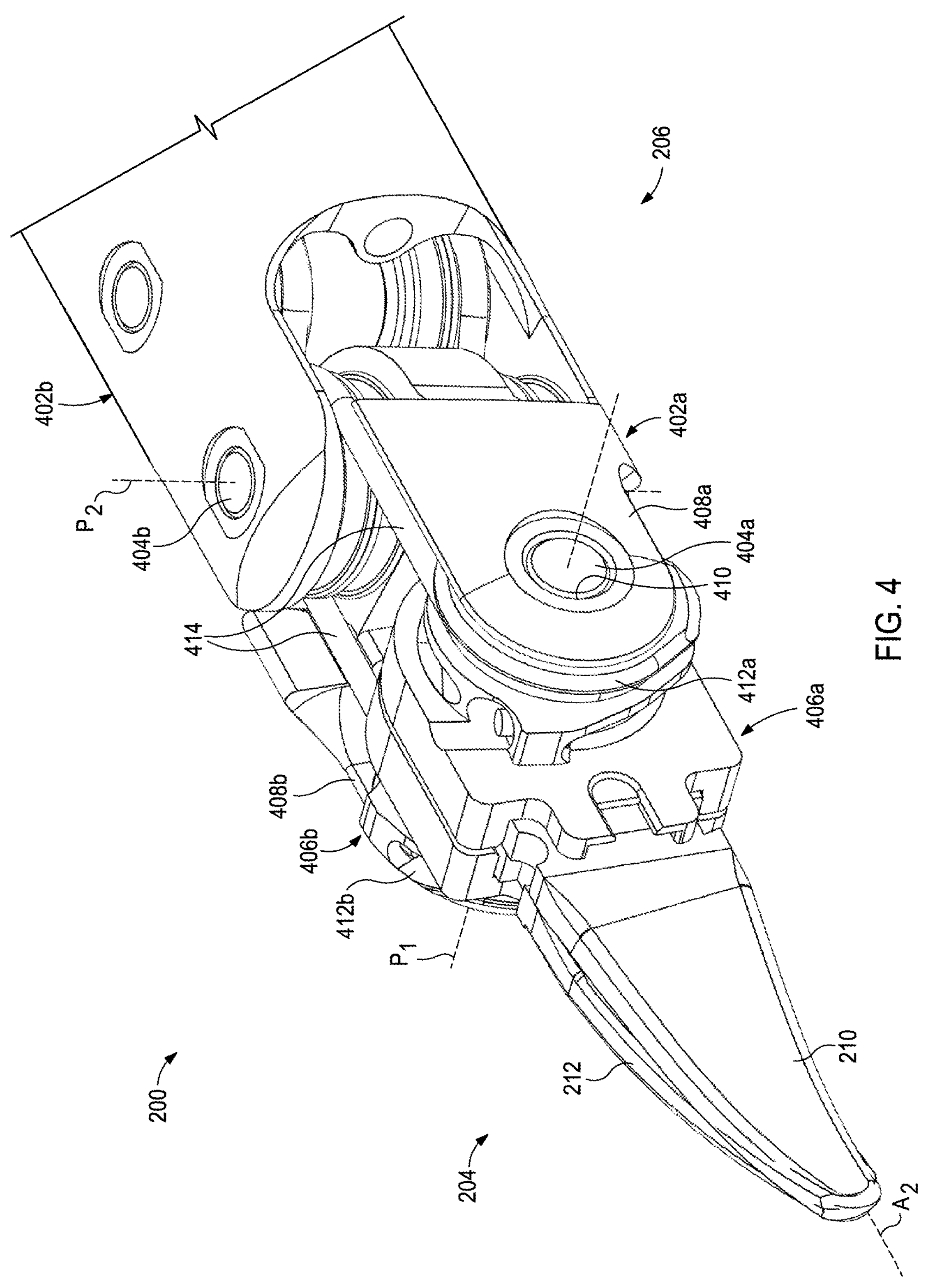
FIG. 4 is an enlarged isometric view of the distal end of the surgical tool of FIG. 2.

FIG. 4 is an enlarged isometric view of the distal end of the surgical tool 200, according to one or more embodiments. More specifically, FIG. 4 depicts an enlarged view of the end effector 204 and the wrist 206, with the end effector 204 in the unarticulated position. The end effector 204 is operatively coupled to wrist 206, which includes a distal clevis 402*a* and a proximal clevis 402*b*. The end effector 204 (i.e., the blades 210, 212) is rotatably mounted to the distal clevis 402*a* at a first axle 404*a*, and the distal clevis 402*a* is rotatably mounted to the proximal clevis 402*b* at a second axle 404*b*. The wrist 206 provides a first pivot axis $P_1$ that extends through the first axle 404*a* and a second pivot axis $P_2$ that extends through the second axle 404*b*. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "pitch" articulation of the end effector 204, and movement about the second pivot axis $P_2$ provides "yaw" articulation of the end effector 204.

In some embodiments, as described in more detail below, the first axle 402*a* may comprise two axles axially aligned along the first pivot axis $P_1$. In such embodiments, each independent axle will be associated with a corresponding one of the first and second blades 210, 212. The two independent axles may prove advantageous in allowing the blades 210 to be removed and replaced without disassembling the entire end effector 204 or detaching the end effector from the wrist 206.

In the illustrated embodiment, the blades 210, 212 are actuatable between closed and open positions by movement at the first pivot axis $P_1$. More specifically, the end effector 204 includes first and second blade holders 406*a* and 406*b*, and the blades 210, 212 are releasably coupled to the blade holders 406*a,b*, respectively. The distal clevis 402*a* includes a pair of distally-extending arms 408*a* and 408*b*, and the blade holders 406*a,b* are rotatably mounted to the arms 408*a,b*, respectively. The first axle 404*a* is mounted to corresponding apertures 410 (only one visible) defined in each arm 410*a,b*, and the blade holders 406*a,b* are mounted to the first axle 404*a* and rotatable about the first pivot axis $P_1$. As described below, however, the first axle 404*a* includes two axles axially aligned along the first pivot axis $P_1$, and the first and second blade holders 406*a,b* are rotatably mounted to the corresponding arm 408*a,b* using an associated axle.

Moreover, each blade holder 406*a,b* includes or is otherwise coupled to a corresponding actuation pulley 412*a* and 412*b* such that rotation of the actuation pulleys 412*a,b* correspondingly rotates the blade holder 406*a,b*, and thereby rotates the coupled blades 210, 212. A plurality of drive cables 414 pass through the wrist 206 and terminate at the actuation pulleys 412*a,b*. The drive cables 414 form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 414 can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof.

The drive cables 414 extend proximally from the end effector 204 to the drive housing 208 (FIG. 2) where they are operatively coupled to various actuation mechanisms or devices housed (contained) therein to facilitate longitudinal movement (translation) of the drive cables 414. Selective actuation of all or some of the drive cables 414 causes the wrist 206 to articulate, causes the blades 210, 212 to open or close, or causes a combination of the foregoing. In at least one embodiment, the surgical tool 200 includes four drive cables 414, where a pair of drive cables 414 terminates at each actuation pulley 412*a,b*. The pairs of drive cables 414 may be configured to "antagonistically" operate to move the corresponding blades 210, 212. Accordingly, the drive cables 414 may be characterized or otherwise referred to as "antagonistic" cables that cooperatively (yet antagonistically) operate to cause relative or tandem movement of the blade holders 406*a,b* and, therefore, relative or tandem movement of the blades 210, 212.

Figure 5A:
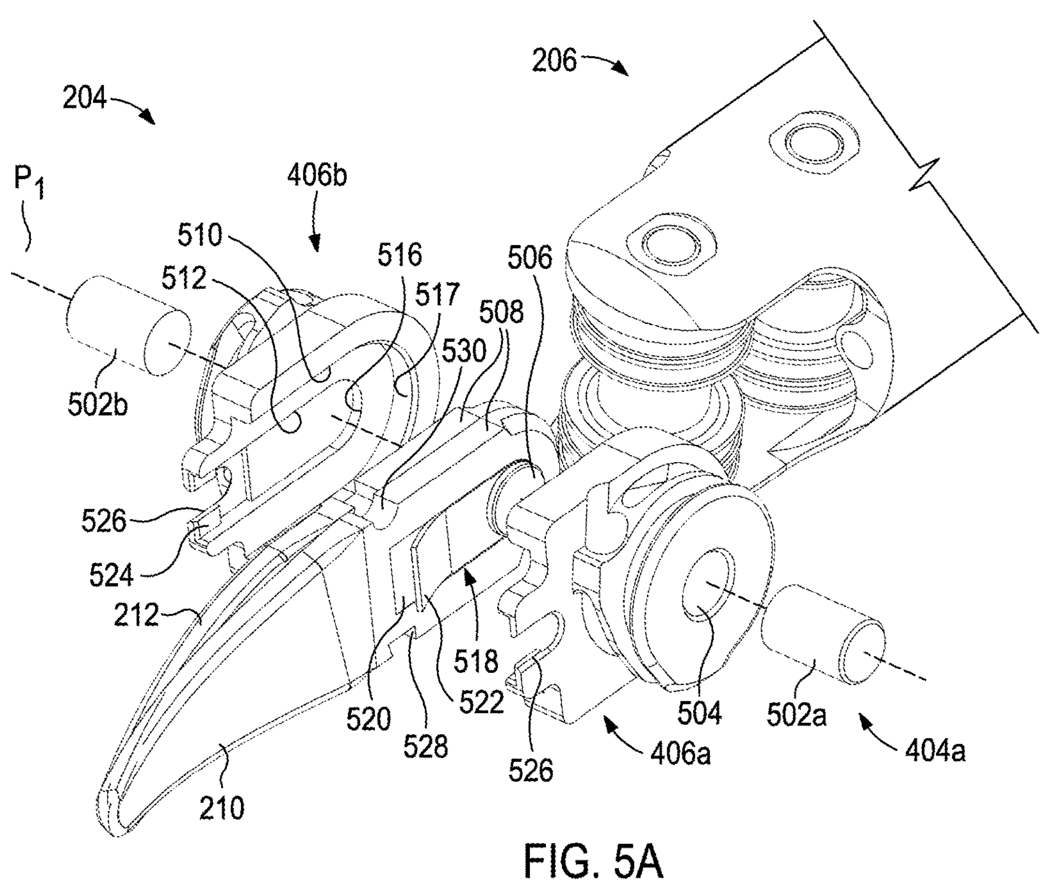
FIGS. 5A and 5B are right and left isometric views, respectively, of portions of the end effector and the wrist, according to one or more embodiments.
Figure 5B:
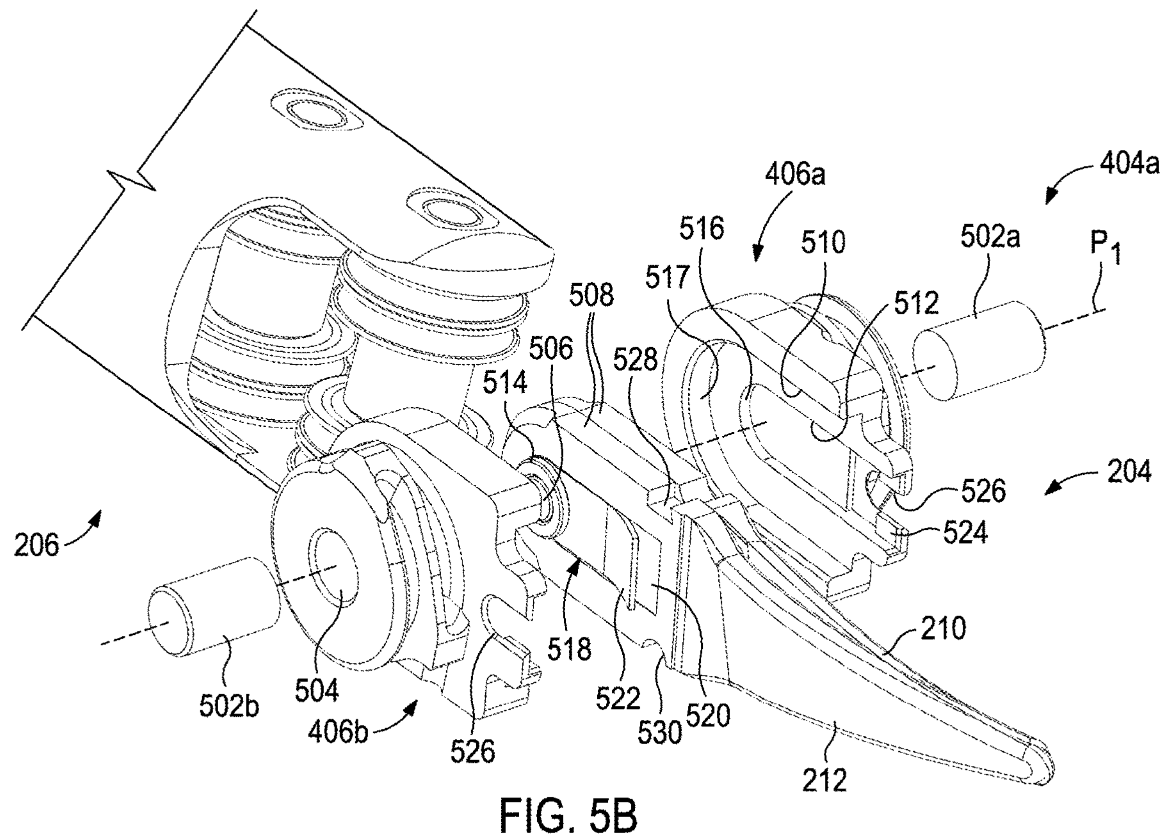

FIGS. 5A and 5B are right and left isometric views, respectively, of portions of the end effector 204 and the wrist 206, with the end effector 204 exploded, according to one or more embodiments. The distal clevis 402*a* (FIG. 4) and the drive cables 414 (FIG. 4) are omitted in FIGS. 5A-5B to enable viewing of various internal structures of the end effector 204.

As illustrated, the first axle 404*a* comprises two axle portions, shown as a first axle portion 502*a* and a second axle portion 502*b*. The first axle portion 502*a* may be configured to rotatably mount the first blade holder 406*a* to the first arm 408*a* (FIG. 4) of the distal clevis 402*a* (FIG. 4), and the second axle portion 502*b* may be configured to rotatably mount the second blade holder 406*b* to the second arm 408*b* (FIG. 4) of the distal clevis 402*a*. As illustrated, each blade holder 406*a,b* may define an axle aperture 504 sized to receive the corresponding axle portion 502*a,b*. The first pivot axis $P_1$ extends through the first axle 404*a* and, more particularly, through the axle portions 502*a,b* when the blade holders 406*a,b* are rotatably mounted to the distal clevis 402*a*.

The blades 210, 212 may be pinned and otherwise rotatably coupled to each other using a center pin 506. More particularly, each blade 210, 212 may include or otherwise provide a shank 508 that extends proximally from the cutting portion of each blade 210, 212, and the center pin 506 may extend through coaxially aligned apertures (not shown) defined in each shank 508. When the blades 210, 212 are properly mounted to the blade holders 406*a,b*, and the blade holders 406*a,b* are mounted to the distal clevis 402*a* (FIG. 4), the first pivot axis $P_1$ will extend through the center pin 506. Consequently, during operation of the end effector 204, rotation (actuation) of the blade holders 406*a,b* will correspondingly cause the blades 210, 212 to rotate about the first pivot axis $P_1$ between open and closed positions.

As illustrated, each blade holder 406*a,b* defines and otherwise provides an elongated and open-ended blade channel 510 (open in the distal direction), where each blade channel 510 is sized to receive the shank 508 of the laterally adjacent blade 210, 212. Moreover, each blade holder 406*a,b* may further define an elongated and open-ended pin slot 512 (open in the distal direction) defined within (e.g., recessed into) the blade channel 510 and sized to receive portions of the center pin 506 on opposing sides of each shank 508. In some applications, as best seen in FIG. 5B, the center pin 506 may be secured in place using a washer 514, and the head of the center pin 506 and the washer 514 may be sized to be received within the laterally adjacent pin slots 512.

In some embodiments, as illustrated, each pin slot 512 may terminate with an arcuate or curved profile 516, and the blades 210, 212 may be advanced into the blade channels 510 until the center pin 506 (or the washer 514) engages the curved profile 516. In other embodiments, or in addition thereto, each blade channel 510 may terminate with an arcuate or curved profile 517, and the blades 210, 212 may be advanced into the blade channels 510 until the proximal end of each shank 508 engages the curved profile 517.

Each blade 210, 212 may have a securing device 518 mounted thereto and configured to secure the corresponding blade 210, 212 to the respective blade holder 406*a,b* when the blades 210, 212 are received within the blade channels 510. In the illustrated embodiment, each securing device 518 comprises a leaf spring mounted to the shank 508 of the corresponding blade 210, 212. In such embodiments, rotatably coupling the blades 210, 212 with the center pin 506 may also secure the securing device 518 to the blades 210, 212. In other embodiments, however, the securing device 518 may comprise other types of devices, mechanisms, or apparatus operable to secure the corresponding blade 210, 212 to the adjacent blade holder 406*a,b*. In embodiments where the securing device 518 comprises a leaf spring, the securing device 518 may be received within a recess 520 defined in the lateral side of the corresponding shank 508. In at least one embodiment, the securing device 518 may be received within the recess 520 such that it sits generally flush with the adjacent portions of the shank 508.

The securing device 518 may include or otherwise provide a latching feature 522 arranged to locate and engage a projected shoulder 524 defined within the pin slot 512 of each blade holder 406*a,b*. The latching feature 522 may be spring biased to naturally project laterally outward from the shank 508 and away from the recess 520. In such embodiments, the securing device 518 may be made of spring steel or a compliant plastic material capable of naturally biasing the latching feature 522 laterally outward. In operation, as the blades 210, 212 are inserted into the blade channels 510 and advanced proximally, the latching feature 522 will be biased laterally inward and into the corresponding recess 520 until eventually bypassing and locating the projected shoulder 524, at which point the latching feature 522 will be able to spring laterally outward to engage the projected shoulder 524. Engaging the latching feature 522 against the projected shoulder 524 axially secures the blades 210, 212 to the blade holders 406*a,b* and, more particularly, within the blade channels 510.

In some embodiments, each blade holder 406*a,b* may define a latch aperture 526 at or near its distal end. In at least one embodiment, as illustrated, one or both of the latch apertures 526 may be open-ended in the proximal direction, but could alternatively be closed. As described in more detail below, the latch aperture 526 may provide a location to access and laterally engage the latching feature 522 to disengage the latching feature 522 (e.g., force it laterally inward) from the projected shoulder 524. Accordingly, when the blades 210, 212 are properly received within the blade holders 406*a,b*, the latching features 522 may be exposed and otherwise accessible through the latch apertures 526.

Each blade 210, 212 includes or defines a disassembly detent 528 and an assembly detent 530. As illustrated, each detent 528, 530 may be provided on the shank 508 of the corresponding blade 210, 212, and may be provided on opposite sides of the shank 508, but could alternatively be provided at other locations on the blades 210, 212. When the blades 210, 212 are properly mounted to the blade holders 406*a,b*, the detents 528, 530 will be exposed and otherwise located outside of the corresponding blade channels 510. As described in more detail below, this helps the blades 210, 212 to be removed from the blade holders 406*a,b* using a disassembly cassette and/or helps a user install new blades on the blade holders 406*a,b* using an assembly cassette. More specifically, each disassembly detent 528 may be engageable with a blade retention feature 710 (FIG. 7C) included in the disassembly cassette. Moreover, each assembly detent 530 may be engageable with a blade camming feature 904 (FIG. 9B) included in the assembly cassette.

Figure 6A:
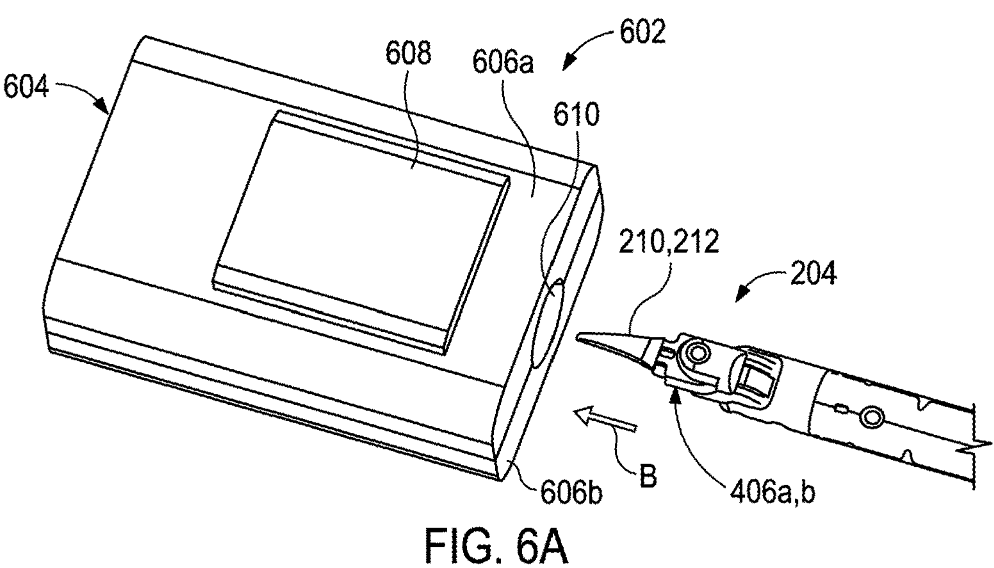
FIGS. 6A-6C are isometric views showing progressive steps of removing the blades from the end effector 204, according to one or more embodiments of the present disclosure.
Figure 6B:
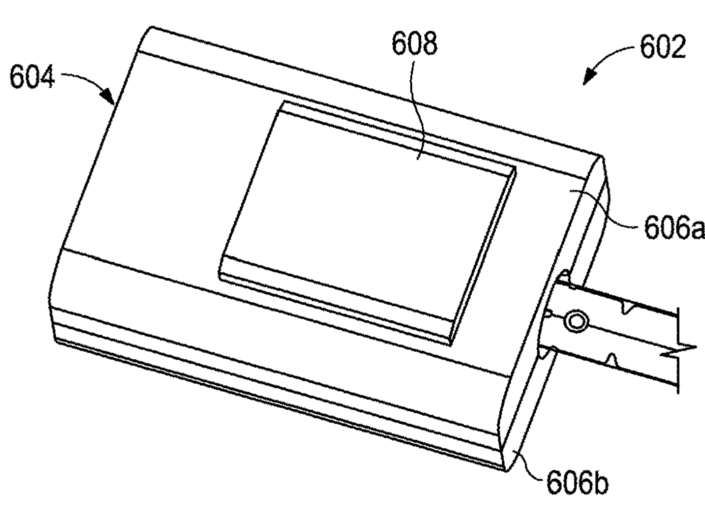
Figure 6C:
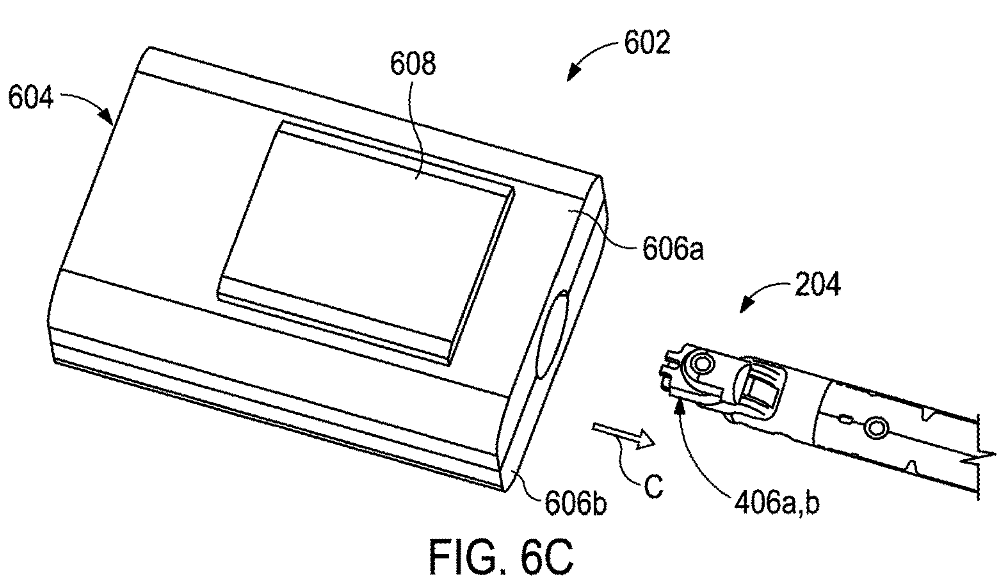

FIGS. 6A-6C are isometric views showing progressive steps of removing the blades 210, 212 from the end effector 204, according to one or more embodiments of the present disclosure. In some embodiments, as illustrated, a disassembly cassette 602 may be used to remove the blades 210, 212. The disassembly cassette 602 includes a rigid body 604 capable of being handled by a user (e.g., a service technician, a bedside nurse, a surgeon, etc.) to manually remove the blades 210, 212 from the blade holders 406*a,b*. In other embodiments, however, the disassembly cassette 602 may be secured to a substrate, such as a table or another working surface.

As illustrated, the body 604 may exhibit a generally rectangular cross-section or shape, but could alternatively exhibit other geometries or shapes, without departing from the scope of the disclosure. In some embodiments, the body 604 may include a first or "upper" half 606*a* and a second or "lower" half 606*b* removably coupled to each other. A detachment button 608 may be mounted to each half 606*a,b* (only one detachment button 608 visible) and may be pressed (actuated) to release the blades 210, 212 from the corresponding blade holders 406*a,b*. In some embodiments, the detachment buttons 608 may be spring-loaded and naturally biased to an outwardly projected position; e.g., projected past the outer surface of the corresponding half 606*a,b*.

Referring first to FIG. 6A, the upper and lower halves 606*a,b* may cooperatively define an insertion aperture 610 sized to receive the end effector 204. To remove the blades 210, 212, a user axially aligns the end effector 204 with the insertion aperture 610 and advances the end effector 204 into the insertion aperture 610 in the direction B. In some embodiments, the insertion aperture 610 may include or otherwise define one or more camming features (not shown) that help angularly orient the end effector 204 for proper insertion into the interior of the disassembly cassette 602. In other embodiments, however, the user may need to rotate the end effector 204 to properly orient the end effector 204 for full insertion into the disassembly cassette 602.

In FIG. 6B, the end effector 204 is advanced fully into the disassembly cassette 602. In some embodiments, the end effector 204 is advanced until engaging a stop shoulder (not shown) or the like, thereby preventing further distal advancement of the end effector 204. Once the end effector 204 is properly advanced into the disassembly cassette 602, the user may press (actuate) both detachment buttons 608 (only one visible) either simultaneously or in sequence. Pressing the detachment buttons 608 actuates internal features of the disassembly cassette 602, which detaches the blades 210, 212 from the blade holders 406*a,b*.

In FIG. 6C, the end effector 204 is withdrawn from the disassembly cassette 602, as shown by the direction arrow C. The used blades 210, 212 are retained within the interior of the disassembly cassette 602. At this point, new blades can be secured (coupled) to the blade holders 406*a,b*, if desired.

Figure 7A:
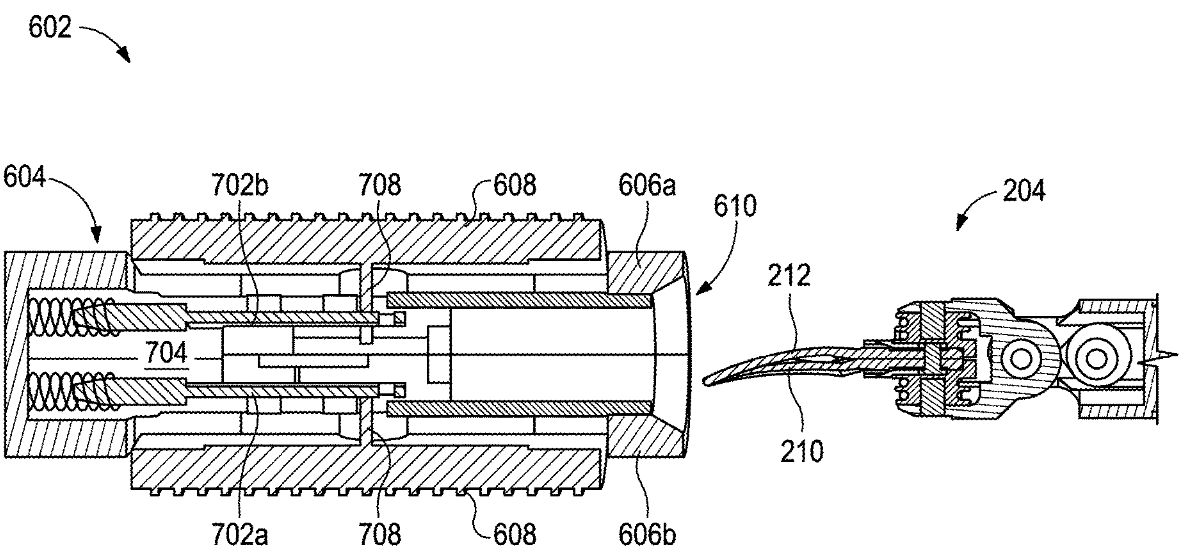
FIGS. 7A-7C are cross-sectional and personal cross-sectional side views of progressive steps in removing the blades using the disassembly cassette of FIGS. 6A-6C, according to one or more embodiments.
Figure 7B:
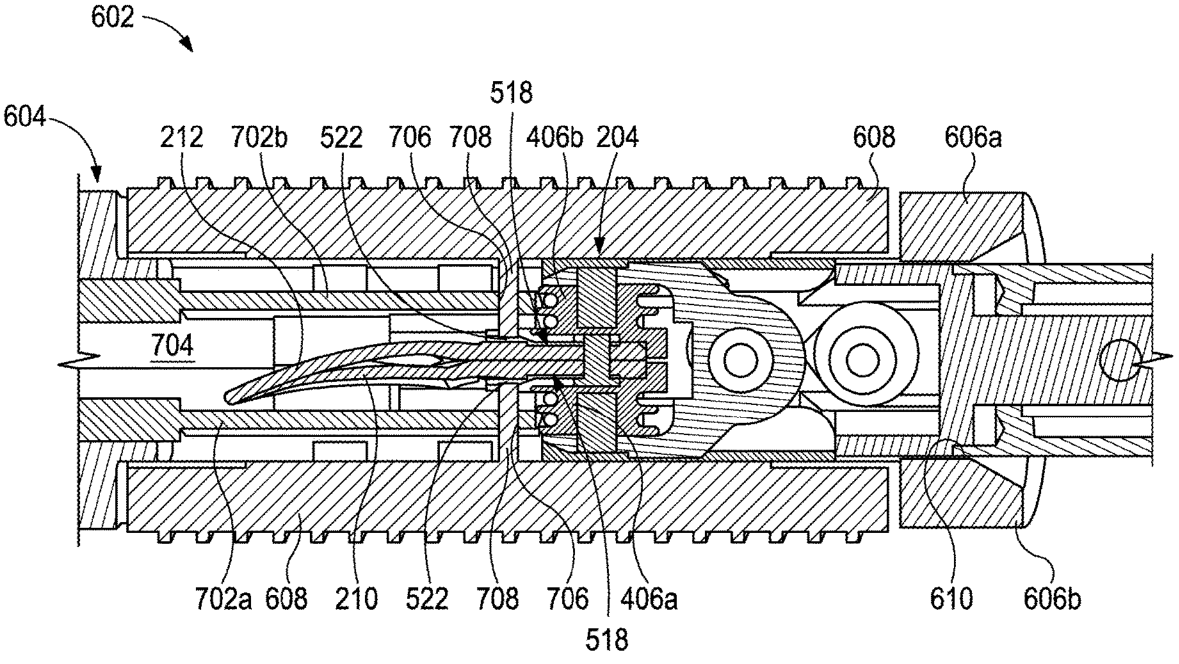
Figure 7C:
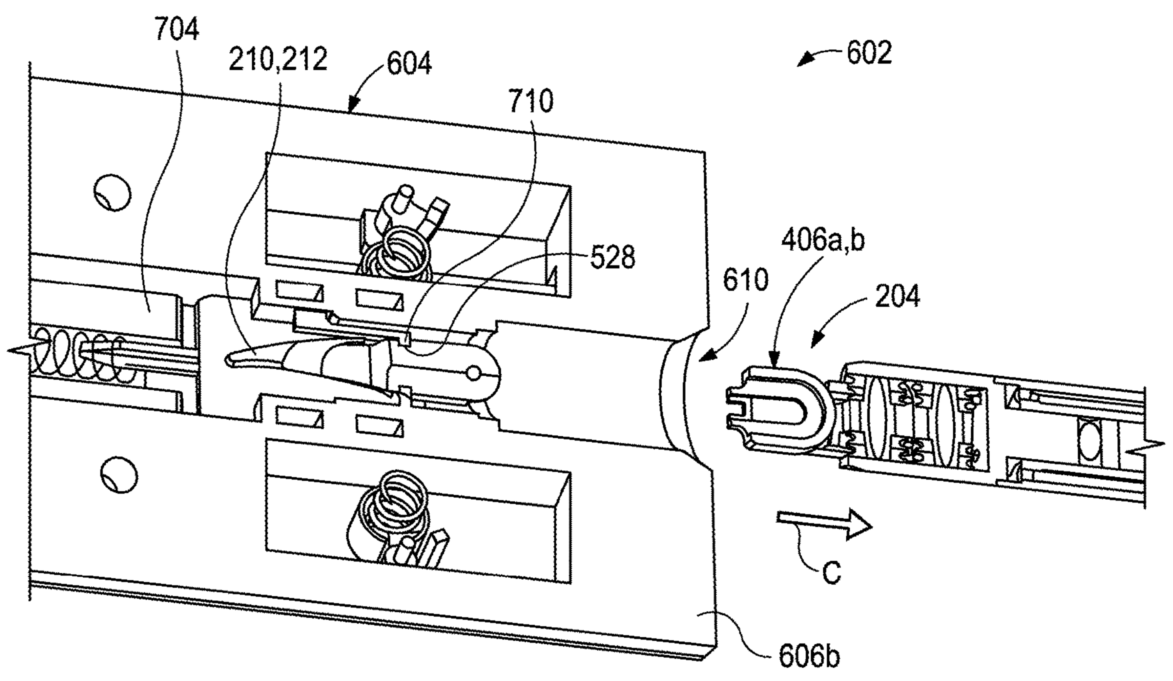

FIGS. 7A-7C are cross-sectional and partial cross-sectional side views showing progressive steps in removing the blades 210, 212 using the disassembly cassette 602, according to one or more embodiments. As discussed above, the body 604 of the disassembly cassette 602 includes the upper and lower halves 606*a,b*, which cooperatively define the insertion aperture 610. Moreover, a detachment button 608 may be mounted to each half 606*a,b* and may be actuatable between a first or "projected" position, as shown in FIG. 7A, and a second or "depressed" position, as shown in FIG. 7B. The detachment buttons 608 may be spring-biased and, therefore, naturally biased to the projected position.

Referring first to FIG. 7A, in some embodiments, the disassembly cassette 602 may further include first and second insertion lockout members 702*a* and 702*b* arranged within an interior 704 of the body 604, which is cooperatively defined by the upper and lower halves 606*a,b* when the halves 606*a,b* are coupled. The insertion lockout members 702*a,b* may be longitudinally movable within the interior 704 upon insertion of the end effector 204 into the interior 704 via the insertion aperture 610.

As illustrated, each insertion lockout member 702*a,b* defines an aperture 706 sized to receive an adjacent disengagement post 708 extending laterally inward from each detachment button 608. The insertion lockout members 702*a,b* are movable (actuatable) between a first or "blocking" position, as shown in FIG. 7A, where the apertures 706 are misaligned with the adjacent disengagement posts 708, and a second or "aligned" position, as shown in FIG. 7B, where the apertures 706 align with the adjacent disengagement posts 708. When the insertion lockout members 702*a,b* are in the blocking position, the detachment buttons 608 are prevented from transitioning from the projected position to the depressed position since the disengagement posts 708 will bind against the adjacent insertion lockout member 702*a,b*. However, once the insertion lockout members 702*a,b* are transitioned to the aligned position, the apertures 706 will align with the adjacent disengagement posts 708, thereby allowing the detachment buttons 608 to transition to the depressed position.

In FIG. 7B, the end effector 204 has been inserted into the interior 704 of the disassembly cassette 602 via the insertion aperture 610. As the end effector 204 enters the interior 704, the insertion lockout members 702*a,b* are transitioned from the blocking position to the aligned position. More specifically, the insertion lockout member 702*a,b* may be arranged to engage the blade holders 406*a,b* (or another structural part of the end effector 204) as the end effector 204 is advanced into the disassembly cassette 602. Advancing the end effector 204 further into the disassembly cassette 602 will cause the insertion lockout members 702*a,b* to move (transition) to the aligned position, where the apertures 706 align with the adjacent disengagement posts 708. This allows the disengagement posts 708 to be received within the apertures 706 as the detachment buttons 608 are depressed (actuated) laterally inward and to the depressed position, as shown in FIG. 7B.

As mentioned above, in some embodiments, the detachment buttons 608 may be manually pressed by a user. In such embodiments, the user may manually grasped the detachment cassette 602 and simultaneously (or sequentially) press the detachment buttons 608, such as between the forefinger and thumb of the hand. In other embodiments, however, actuation of one or both of the detachment buttons 608 may be automated.

As the detachment buttons 608 are advanced to the depressed position, the disengagement posts 708 are simultaneously advanced through the apertures 706 and into lateral engagement with the latching features 522 of the adjacent securing devices 518. Applying a lateral load on the latching features 522 via the disengagement posts 708 causes the latching features 522 to flex out of engagement with the corresponding projected shoulder 524 (FIGS. 5A-5B), thereby releasing (unlatching) the blades 210, 212 from the corresponding blade holders 406*a,b*. Once the blades 210, 212 are released from the blade holders 406*a,b*, the end effector 204 may be reversed out of the disassembly cassette 602, leaving the used blades 210, 212 within the interior 704.

FIG. 7C is an isometric, partial cross-sectional view of the disassembly cassette 602 and the end effector 204. As illustrated, the end effector 204 is shown reversed out of the disassembly cassette 602 in the direction C. In some embodiments, a blade retention feature 710 may be provided and otherwise defined within the interior 704 of the disassembly cassette 602. The blade retention feature 710 may be configured to locate and be received within the disassembly detent 528 defined on the adjacent blade 210, 212 as the end effector 204 is advanced into the interior 704 of the disassembly cassette 602. In some embodiments, the blade retention feature 710 may form part of a flexible living hinge or the like capable of flexing away from the blades 210, 212 as the end effector 204 is advanced into the interior 704, but able to spring inward to be received within the disassembly detent 528 upon locating the disassembly detent 720. In at least one embodiment, the user may hear an audible "click" when the blade retention feature 710 is received within the disassembly detent 528, thereby indicating that the blades 210, 212 are secured against removal from the disassembly cassette 602.

While only one blade retention feature 710 is shown in FIG. 7C, it will be appreciated that a second blade retention feature 710 will be provided to engage the other blade 210, 212. Receiving the blade retention features 710 in the corresponding disassembly detents 528 secures the blades 210, 212 within the interior 704 of the disassembly cassette 602. Once the latching features 522 (FIGS. 5A-5B and 7B) are forced out of engagement with the corresponding projected shoulders 524 (FIGS. 5A-5C), as generally described above with reference to FIG. 7B, the end effector 204 may then be withdrawn in the direction C. As the end effector 204 moves in the direction C, the blade holders 406*a,b* will separate from the blades 210, 212, which are secured within the interior 704 using the blade retention features 710.

Figure 8A:
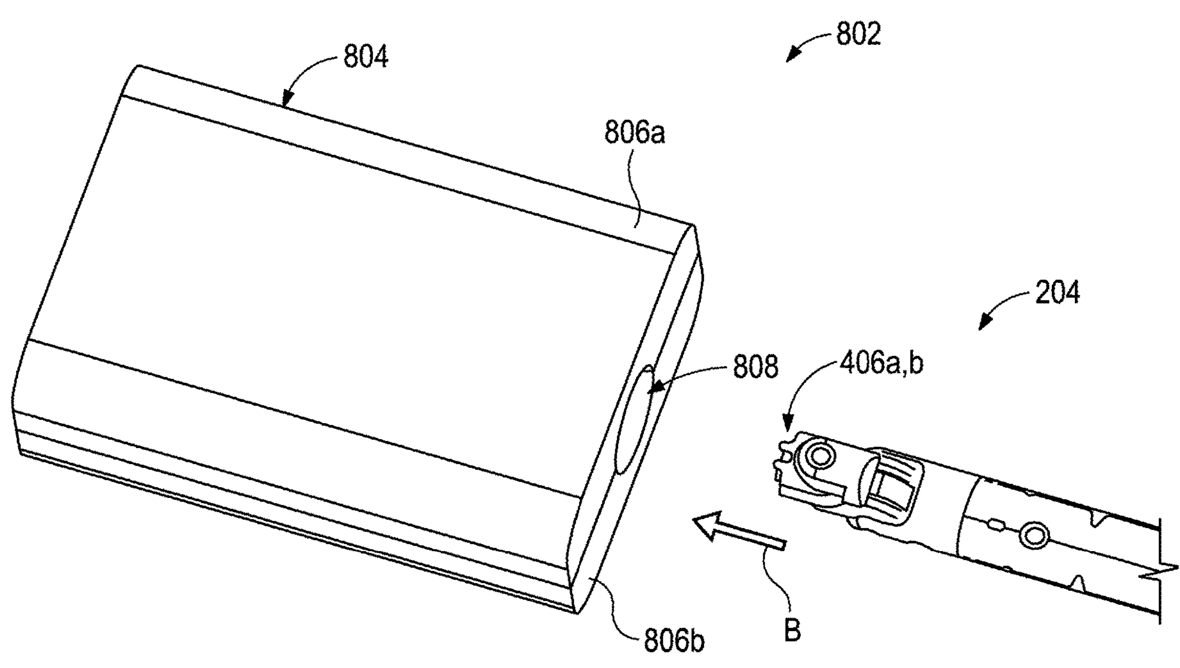
FIGS. 8A-8C are isometric views showing progressive steps of installing new blades on the end effector, according to one or more embodiments of the present disclosure.
Figure 8B:
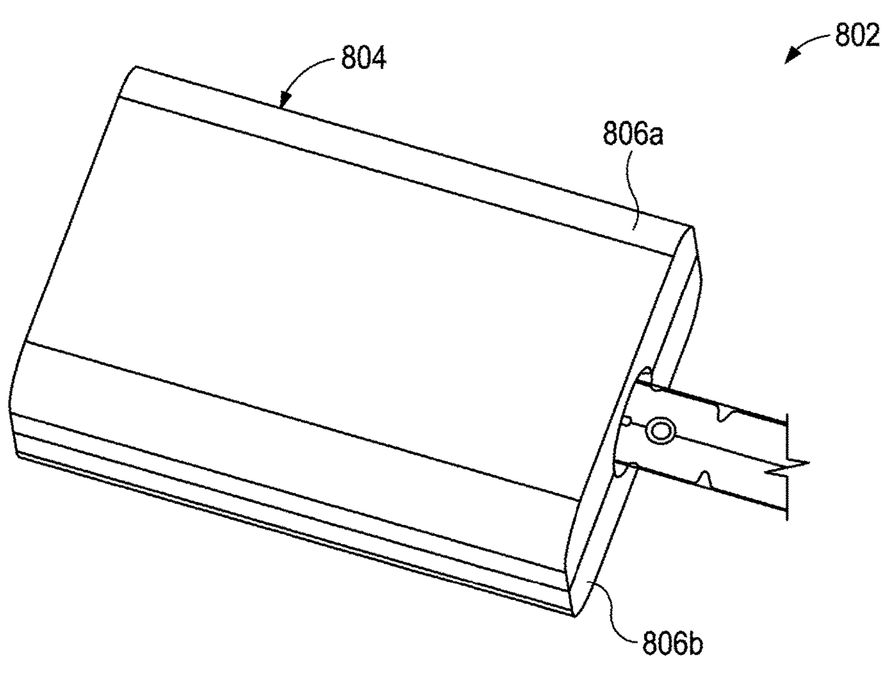
Figure 8C:
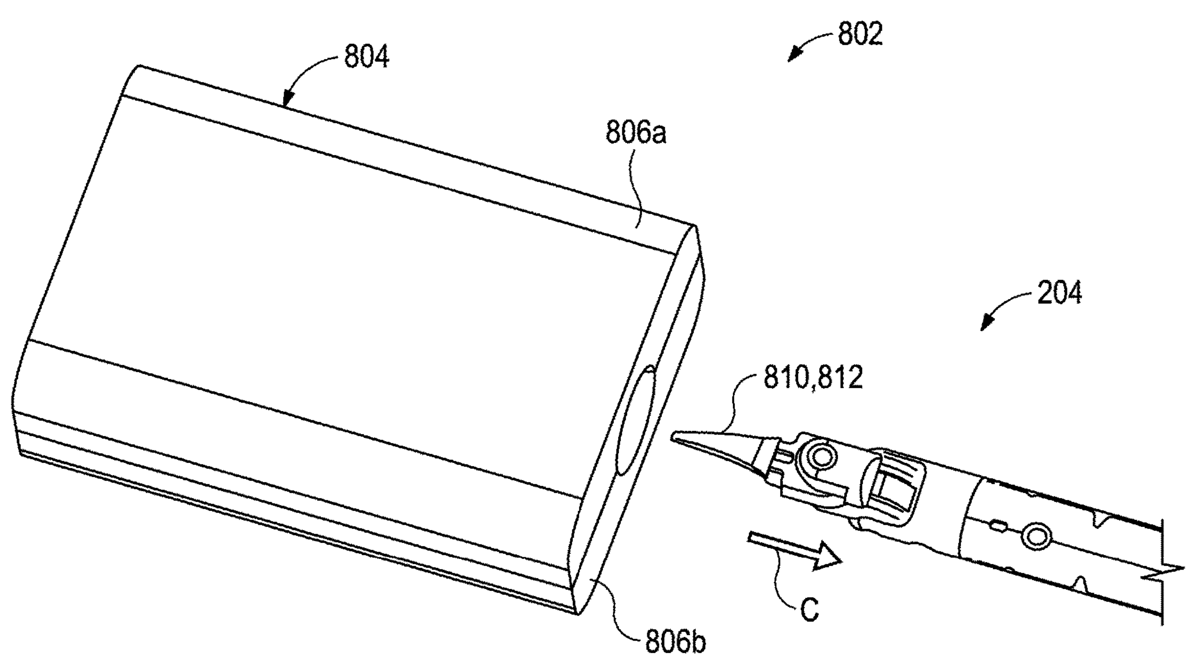

FIGS. 8A-8C are isometric views showing progressive steps of installing new blades on the end effector 204, according to one or more embodiments of the present disclosure. In some embodiments, as illustrated, an assembly cassette 802 may be used to install new blades on the end effector 204. Similar to the disassembly cassette 602 (FIGS. 6A-6C), the assembly cassette 802 includes a rigid body 804 capable of being handled by a user (e.g., a service technician, a bedside nurse, a surgeon, etc.), and the body 804 may include a first or "upper" half 806*a* and a second or "lower" half 806*b* removably coupled to the upper half 806*a*. Moreover, the body 804 may exhibit a generally rectangular cross-section or shape, but could alternatively exhibit other geometries or shapes, without departing from the scope of the disclosure. The new blades (not visible) may be preinstalled within the interior of the assembly cassette 802.

Referring first to FIG. 8A, the upper and lower halves 806*a,b* may cooperatively define an insertion aperture 808 sized to receive the end effector 204. To install the new blades on the blade holders 406*a,b*, a user will align the end effector 204 with the insertion aperture 808 and advance the end effector 204 into the insertion aperture 808 in the direction B. In some embodiments, the insertion aperture 808 may include or otherwise define one or more camming features (not shown) that angularly orient the end effector 204 for proper insertion into the interior of the assembly cassette 802. In other embodiments, however, the user may need to rotate the end effector 204 manually to properly orient the end effector 204 for proper insertion into the assembly cassette 802.

In FIG. 8B, the end effector 204 is advanced fully into the assembly cassette 802. In some embodiments, the end effector 204 is advanced until engaging a stop shoulder (not shown) or the like, thereby preventing further distal advancement of the end effector 204. Advancing the end effector 204 fully into the assembly cassette 802 will automatically attach the new blades (not shown) to the blade holders 406*a,b*. In some embodiments, the user may hear an audible "click" indicating that the new blades have been properly seated on blade holder 406*a,b*.

In FIG. 8C, the end effector 204, including newly installed first and second blades 810, 812, is withdrawn from the assembly cassette 802 in the direction C. At this point, the end effector 204 may be used in subsequent operations surgical procedures.

Figure 9A:
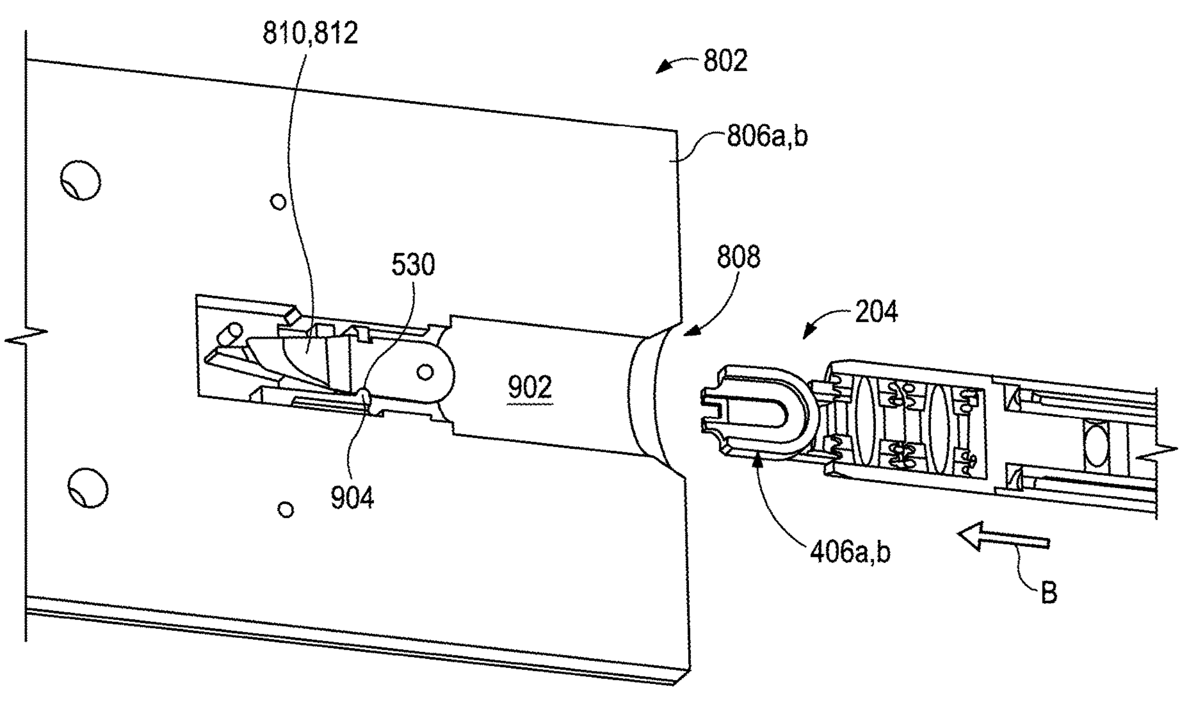
FIGS. 9A and 9B are partial cross-sectional views showing progressive steps in installing the new blades using the assembly cassette of FIGS. 8A-8C, according to one or more embodiments.
Figure 9B:
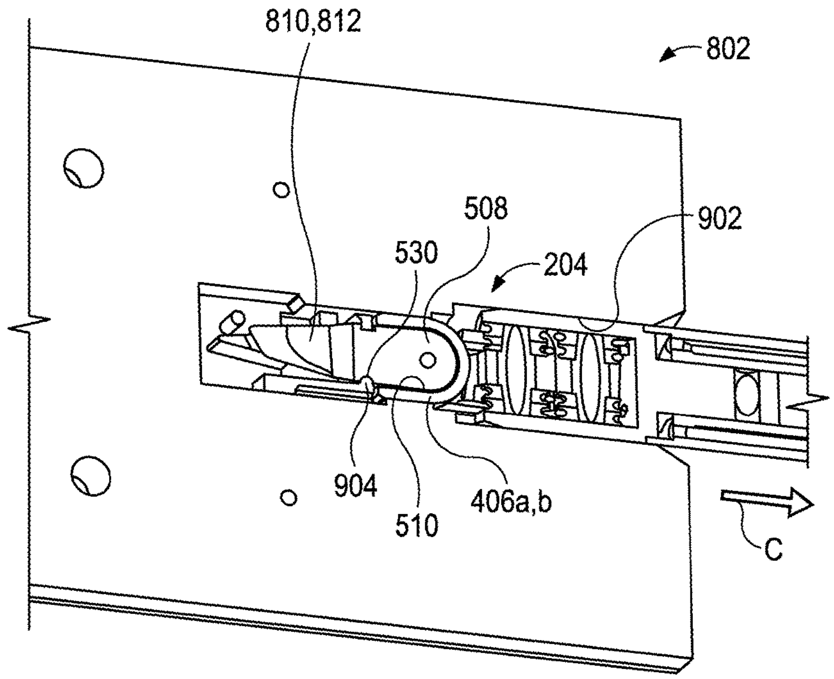

FIGS. 9A and 9B are partial cross-sectional views showing progressive steps for installing the new blades 810, 812 using the assembly cassette 802, according to one or more embodiments. The new blades 810, 812 may be substantially similar to the used blades 210, 212, accordingly reference numerals used with respect to the used blades 210, 212 will be used with respect to the new blades 810, 812 and will refer to similar component parts.

Referring first to FIG. 9A, the new blades 810, 812 may be preinstalled and otherwise arranged within an interior 902 of the assembly cassette 802. The interior 902 may be cooperatively defined by the upper and lower halves 806*a,b* and may be accessible via the insertion aperture 808. In some embodiments, a blade camming feature 904 may be provided and otherwise defined within the interior 902 of the assembly cassette 802 and configured to secure the blades 810, 812 within the interior 902. More specifically, the blade camming feature 904 may be received within the assembly detent 530 provided on the new blades 810, 812. While only one blade camming feature 904 is shown in FIG. 9A engaging only one of the blades 810, 812, it will be appreciated that a second blade camming feature 904 will be provided to engage the other blade 810, 812.

To install the new blades 810, 812 on the end effector 204 and, more particularly on the blade holders 406*a,b*, the end effector 204 may be advanced into the interior 902 via the insertion aperture 808 in the direction B.

In FIG. 9B, the end effector 204 is advanced into the interior 902 until the blades 810, 812 are received within the corresponding blade holders 406*a,b*. As the end effector 204 is advanced into the interior 902, the shanks 508 of the new blades 810, 812 may be received within the open-ended blade channels 510 of each blade holder 406*a,b*. As the blades 810, 812 are inserted into the blade channels 510 and advanced further, the latching feature 522 (FIGS. 5A-5B) will be biased laterally inward until eventually bypassing and locating the projected shoulder 524 (FIGS. 5A-5B), at which point the latching feature 522 will be able to spring laterally outward to engage the projected shoulder 524. Engaging the latching feature 522 against the projected shoulder 524 axially secures the blades 810, 812 to the blade holders 406*a,b* and, more particularly, within the blade channels 510.

At this point, the end effector 204 may be withdrawn from the assembly cassette 802 in the direction C. As the end effector 204 moves in the direction C, the blade camming feature 904 will flex out of engagement with the assembly detent 530, thereby allowing the blades 810, 812 to exit the interior 902. The blade camming feature 904 may form part of a flexible living hinge or the like capable of flexing away from the blades 210, 212 as the end effector 204 is advanced out of the interior 902. The latching or securing engagement between the latching feature 522 (FIGS. 5A-5B) and the projected shoulder 524 (FIGS. 5A-5B), may be greater than the securing engagement between the blade camming feature 904 and the assembly detent 530. In at least one embodiment, for example, the assembly detent 530 may be curved and otherwise arcuate, thereby providing a camming surface that the blade camming feature 904 may easily exit with sufficient axial force. Consequently, pulling on the end effector 204 and the proximal direction C, will flex the camming feature 904 out of engagement with the assembly detent 530.

With reference to FIGS. 6A-6C and FIGS. 8A-8C, it is contemplated herein to provide a combined or "universal" cassette that includes all of the features of the disassembly and assembly cassettes 602, 802. In particular, it is contemplated herein to provide a universal cassette where all of the features of the disassembly cassette 602 are provided at one end of the universal cassette, and all of the features of the assembly cassette 802 are provided at the opposing end of the universal cassette.

Embodiments disclosed herein include:

A. A surgical tool includes a drive housing, an elongate shaft extending distally from the drive housing, a wrist arranged at a distal end of the shaft and including a distal clevis with first and second distally-extending arms, and an end effector operatively coupled to the wrist and including a first blade holder rotatably mounted to the first arm at a first axle, a second blade holder rotatably mounted to the second arm at a second axle, a first blade releasably coupled to the first blade holder with a first securing device, and a second blade rotatably coupled to the first blade at a center pin and releasably coupled to the second blade holder with a second securing device, wherein disengaging the first and second securing devices from the first and second blade holders allows the first and second blades to be separated from the first and second blade holders.

B. A method of replacing first and second blades of an end effector includes providing a surgical tool that includes the end effector and further includes an elongate shaft extending distally from a drive housing, a wrist arranged at a distal end of the shaft and including first and second distally-extending arms, and an end effector operatively coupled to the wrist and including first and second blade holders rotatably mounted to the first and second arms at first and second axles, respectively, wherein the first blade is releasably coupled to the first blade holder with a first securing device, and the second blade is rotatably coupled to the first blade at a center pin and releasably coupled to the second blade holder with a second securing device. The method further includes disengaging the first and second securing devices from the first and second blade holders, and separating the first and second blades from the first and second blade holders.

C. An end effector for a surgical tool includes a first blade holder rotatably mountable to a first arm of a distal clevis at a first axle, a second blade holder rotatably mountable to a second arm of the distal clevis at a second axle, a first blade releasably coupled to the first blade holder with a first securing device, and a second blade rotatably coupled to the first blade at a center pin and releasably coupled to the second blade holder with a second securing device, wherein the first and second axles and the center pin are coaxially aligned along a pivot axis, and the first and second blade holders and the first and second blades are rotatable about the pivot axis, and wherein disengaging the first and second securing devices from the first and second blade holders allows the first and second blades to be separated from the first and second blade holders.

Each of embodiments A, B, and C may have one or more of the following additional elements in any combination: Element 1: wherein the first and second axles and the center pin are coaxially aligned along a pivot axis, and wherein the first and second blade holders and the first and second blades are rotatable about the pivot axis. Element 2: wherein the first securing device provides a first latching feature arranged to engage a first projected shoulder provided on the first blade holder, and the second securing device provides a second latching feature arranged to engage a second projected shoulder provided on the second blade holder. Element 3: wherein each blade holder includes an open-ended blade channel sized to receive a shank of a laterally adjacent blade of the first and second blades, and an open-ended pin slot defined within the blade channel and sized to receive a portion of the center pin, wherein the first and second projected shoulders are provided in the pin slot. Element 4: wherein each securing device comprises a leaf spring received within a recess defined in a shank of a corresponding one of the first and second blades, and each latching feature is spring biased to naturally project laterally outward from the shank and away from the recess to engage a corresponding one of the first and second projected shoulders. Element 5: wherein each blade holder defines a latch aperture through which the first and second latching features are engageable to disengage the first and second latching features from the first and second projected shoulders, respectively.

Element 6: wherein disengaging the first and second securing devices from the first and second blade holders comprises laterally engaging a first latching feature of the first securing device through a first latch aperture defined in the first blade holder, laterally engaging the second latching feature through a second latch aperture defined in the second blade holder, forcing the first latching feature laterally inward and thereby disengaging the first latching feature from a first projected shoulder provided on the first blade holder, and forcing the second latching feature laterally inward and thereby disengaging the second latching feature from a second projected shoulder provided on the second blade holder. Element 7: wherein disengaging the first and second securing devices from the first and second blade holders comprises inserting the end effector into an insertion aperture defined in a disassembly cassette, and advancing the end effector into an interior of the disassembly cassette, depressing a first detachment button provided on a first side of the disassembly cassette and thereby disengaging a first latching feature of the first securing device from a first projected shoulder provided on the first blade holder, depressing a second detachment button provided on a second side of the disassembly cassette and thereby disengaging a second latching feature of the second securing device from a second projected shoulder provided on the second blade holder, and withdrawing the end effector from the disassembly cassette while the first and second blades remain within the interior. Element 8: wherein the disassembly cassette includes first and second insertion lockout members arranged within the interior and each defining an aperture sized to receive a disengagement post provided by a corresponding one of the first and second detachment buttons, the method further comprising engaging the first and second lockout members as the end effector advances into the interior of the disassembly cassette, moving, with the end effector, each insertion lockout member from a blocking position, where the aperture is misaligned with the disengagement post, to an aligned position, where the aperture aligns with the disengagement post, depressing the first detachment button and thereby advancing the disengagement post of the first detachment button through the aperture of the first insertion lockout member and engaging the first latching feature, and depressing the second detachment button and thereby advancing the disengagement post of the second detachment button through the aperture of the second insertion lockout member and engaging the second latching feature. Element 9: further comprising receiving a first blade retention feature provided in the interior within a first disassembly detent defined on the first blade, receiving a second blade retention feature provided in the interior within a second disassembly detent defined on the second blade, and retaining the first and second blades within the interior with the first and second retention features as the end effector withdraws from the disassembly cassette. Element 10: further comprising inserting the end effector without the first and second blades into an insertion aperture defined in an assembly cassette, and advancing the end effector into an interior of the assembly cassette, wherein new first and second blades are pre-installed within the assembly cassette, attaching the new first and second blades to the first and second blade holders, respectively, as the end effector advances into the interior, and withdrawing the end effector from the assembly cassette with the new first and second blades attached to the first and second blade holders, respectively. Element 11: wherein first and second blade camming features are provided within the interior, and wherein inserting the end effector without the first and second blades into the insertion aperture is preceded by securing the new first blade within the interior by receiving the first blade camming feature within a first assembly detent defined on the new first blade, and securing the new second blade within the interior by receiving the second blade camming feature within a second assembly detent defined on the new second blade. Element 12: wherein attaching the new first and second blades to the first and second blade holders, respectively, comprises engaging a first latching feature coupled to the new first blade against a first projected shoulder provided on the first blade holder, and thereby securing the new first blade to the first blade holder, and engaging a second latching feature coupled to the new second blade against a second projected shoulder provided on the second blade holder, and thereby securing the new second blade to the second blade holder. Element 13: wherein each blade holder includes an open-ended blade channel and an open-ended pin slot defined within the blade channel, the method further comprising receiving a first shank of the new first blade in the blade channel of the first blade holder, receiving a second shank of the new second blade in the blade channel of the second blade holder, and receiving portions of the center pin in the pin slot of the first and second blade holders, wherein the first and second projected shoulders are provided in the pin slots of the first and second blade holders, respectively.

Element 14: wherein the first securing device provides a first latching feature arranged to engage a first projected shoulder provided on the first blade holder, and the second securing device provides a second latching feature arranged to engage a second projected shoulder provided on the second blade holder. Element 15: wherein each blade holder includes an open-ended blade channel sized to receive a shank of a laterally adjacent blade of the first and second blades, and an open-ended pin slot defined within the blade channel and sized to receive a portion of the center pin, wherein the first and second projected shoulders are provided in the pin slot. Element 16: wherein each securing device comprises a leaf spring received within a recess defined in the shank of the laterally adjacent blade of the first and second blades, and each latching feature is spring biased to naturally project laterally outward from the shank and away from the recess to engage a corresponding one of the first and second projected shoulders. Element 17: wherein each blade holder defines a latch aperture through which the first and second latching features are engageable to disengage the first and second latching feature from the first and second projected shoulders, respectively.

By way of non-limiting example, exemplary combinations applicable to A, B, and C include: Element 2 with Element 3; Element 2 with Element 4; Element 2 with Element 5; Element 7 with Element 8; Element 7 with Element 9; Element 10 with Element 11; Element 10 with Element 12; Element 12 with Element 13; Element 14 with Element 15; Element 14 with Element 16; and Element 14 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
- a drive housing;
- an elongate shaft extending distally from the drive housing;
- a wrist arranged at a distal end of the shaft and including a distal clevis with first and second distally-extending arms; and
- an end effector operatively coupled to the wrist and including:
  - a first blade holder rotatably mounted to the first arm at a first axle;
  - a second blade holder rotatably mounted to the second arm at a second axle independent of the first axle, wherein the first and second blade holder each include:
    - an open-ended blade channel sized to receive a shank of a laterally adjacent blade of first and second blades; and
    - an open-ended pin slot defined within the blade channel and sized to receive a portion of a center pin;
  - the first blade releasably coupled to the first blade holder with a first securing device, wherein the first securing device provides a first latching feature arranged to engage a first projected shoulder provided in the pin slot of the first blade holder; and
  - the second blade rotatably coupled to the first blade at the center pin and releasably coupled to the second blade holder with a second securing device, wherein the second securing device provides a second latching feature arranged to engage a second projected shoulder provided in the pin slot of the second blade holder,
- wherein disengaging the first and second securing devices from the first and second blade holders allows the first and second blades to be separated from the first and second blade holders.

2. The surgical tool of claim 1, wherein the first and second axles and the center pin are coaxially aligned along a pivot axis, and wherein the first and second blade holders and the first and second blades are rotatable about the pivot axis.

3. The surgical tool of claim 1, wherein each securing device comprises a leaf spring received within a recess defined in a shank of a corresponding one of the first and second blades, and each latching feature is spring biased to naturally project laterally outward from the shank and away from the recess to engage a corresponding one of the first and second projected shoulders.

4. The surgical tool of claim 1, wherein each blade holder defines a latch aperture through which the first and second latching features are engageable to disengage the first and second latching features from the first and second projected shoulders, respectively.

5. A method, comprising:
- providing a surgical tool that includes:
  - an elongate shaft extending distally from a drive housing;
  - a wrist arranged at a distal end of the shaft and including first and second distally-extending arms; and
  - an end effector operatively coupled to the wrist and including first and second blade holders rotatably mounted to the first and second arms at first and second axles, respectively,
  - wherein the first and second blade holder each include an open-ended blade channel sized to receive a shank of a laterally adjacent blade of first and second blades, and an open-ended pin slot defined within the blade channel and sized to receive a portion of a center pin,
  - wherein the first and second axles are independent of each other,
  - wherein the first blade is releasably coupled to the first blade holder with a first securing device, and the second blade is rotatably coupled to the first blade at the center pin and releasably coupled to the second blade holder with a second securing device,
  - wherein the first securing device provides a first latching feature arranged to engage a first projected shoulder provided in the pin slot of the first blade holder,
  - wherein the second securing device provides a second latching feature arranged to engage a second projected shoulder provided in the pin slot of the second blade holder;
- disengaging the first and second securing devices from the first and second blade holders; and
- separating the first and second blades from the first and second blade holders.

6. The method of claim 5, wherein disengaging the first and second securing devices from the first and second blade holders comprises:
- laterally engaging a first latching feature of the first securing device through a first latch aperture defined in the first blade holder;
- laterally engaging the second latching feature through a second latch aperture defined in the second blade holder;
- forcing the first latching feature laterally inward and thereby disengaging the first latching feature from the first projected shoulder; and
- forcing the second latching feature laterally inward and thereby disengaging the second latching feature from the second projected shoulder.

7. The method tool of claim 5, wherein disengaging the first and second securing devices from the first and second blade holders comprises:
- inserting the end effector into an insertion aperture defined in a disassembly cassette, and advancing the end effector into an interior of the disassembly cassette;
- depressing a first detachment button provided on a first side of the disassembly cassette and thereby disengaging the first latching feature of the first securing device from the first projected shoulder;
- depressing a second detachment button provided on a second side of the disassembly cassette and thereby disengaging the second latching feature of the second securing device from the second projected shoulder; and
- withdrawing the end effector from the disassembly cassette while the first and second blades remain within the interior.

8. The method of claim 7, wherein the disassembly cassette includes first and second insertion lockout members arranged within the interior and each defining an aperture sized to receive a disengagement post provided by a corresponding one of the first and second detachment buttons, the method further comprising:

engaging the first and second lockout members as the end effector advances into the interior of the disassembly cassette;

moving, with the end effector, each insertion lockout member from a blocking position, where the aperture is misaligned with the disengagement post, to an aligned position, where the aperture aligns with the disengagement post;

depressing the first detachment button and thereby advancing the disengagement post of the first detachment button through the aperture of the first insertion lockout member and engaging the first latching feature; and depressing the second detachment button and thereby advancing the disengagement post of the second detachment button through the aperture of the second insertion lockout member and engaging the second latching feature.

9. The method of claim 7, further comprising:

receiving a first blade retention feature provided in the interior within a first disassembly detent defined on the first blade;

receiving a second blade retention feature provided in the interior within a second disassembly detent defined on the second blade; and retaining the first and second blades within the interior with the first and second retention features as the end effector withdraws from the disassembly cassette.

10. The method of claim 5, further comprising:

inserting the end effector without the first and second blades into an insertion aperture defined in an assembly cassette, and advancing the end effector into an interior of the assembly cassette, wherein new first and second blades are pre-installed within the assembly cassette;

attaching the new first and second blades to the first and second blade holders, respectively, as the end effector advances into the interior; and withdrawing the end effector from the assembly cassette with the new first and second blades attached to the first and second blade holders, respectively.

11. The method of claim 10, wherein first and second blade camming features are provided within the interior of the assembly cassette, and wherein inserting the end effector without the first and second blades into the insertion aperture is preceded by:

securing the new first blade within the interior by receiving the first blade camming feature within a first assembly detent defined on the new first blade; and securing the new second blade within the interior by receiving the second blade camming feature within a second assembly detent defined on the new second blade.

12. The method of claim 10, wherein attaching the new first and second blades to the first and second blade holders, respectively, comprises:

engaging a new first latching feature coupled to the new first blade against the first projected shoulder provided on the first blade holder, and thereby securing the new first blade to the first blade holder; and engaging a new second latching feature coupled to the new second blade against the second projected shoulder provided on the second blade holder, and thereby securing the new second blade to the second blade holder.

13. The method of claim 12, further comprising:

receiving a first shank of the new first blade in the blade channel of the first blade holder;

receiving a second shank of the new second blade in the blade channel of the second blade holder; and receiving portions of the center pin in the pin slot of the first and second blade holders.

14. An end effector for a surgical tool, comprising:

a first blade holder rotatably mountable to a first arm of a distal clevis at a first axle;

a second blade holder rotatably mountable to a second arm of the distal clevis at a second axle independent of the first axle, wherein the first and second blade holder each include:

an open-ended blade channel sized to receive a shank of a laterally adjacent blade of first and second blades; and an open-ended pin slot defined within the blade channel and sized to receive a portion of a center pin;

the first blade releasably coupled to the first blade holder with a first securing device, wherein the first securing device provides a first latching feature arranged to engage a first projected shoulder provided in the pin slot of the first blade holder; and the second blade rotatably coupled to the first blade at the center pin independent of the first and second axles and releasably coupled to the second blade holder with a second securing device, wherein the second securing device provides a second latching feature arranged to engage a second projected shoulder provided in the pin slot of the second blade holder, wherein the first and second axles and the center pin are coaxially aligned along a pivot axis, and the first and second blade holders and the first and second blades are rotatable about the pivot axis, and wherein disengaging the first and second securing devices from the first and second blade holders allows the first and second blades to be separated from the first and second blade holders.

15. The end effector of claim 14, wherein each securing device comprises a leaf spring received within a recess defined in the shank of the laterally adjacent blade of the first and second blades, and each latching feature is spring biased to naturally project laterally outward from the shank and away from the recess to engage a corresponding one of the first and second projected shoulders.

16. The end effector of claim 14, wherein each blade holder defines a latch aperture through which the first and second latching features are engageable to disengage the first and second latching feature from the first and second projected shoulders, respectively.

17. An end effector for a surgical tool, comprising:

a first blade holder rotatably mountable to a first arm of a distal clevis at a first axle;

a second blade holder rotatably mountable to a second arm of the distal clevis at a second axle independent of the first axle;

a first blade releasably coupled to the first blade holder with a first securing device; and a second blade rotatably coupled to the first blade at a center pin independent of the first and second axles and releasably coupled to the second blade holder with a second securing device, wherein the first and second axles and the center pin are coaxially aligned along a pivot axis, and the first and second blade holders and the first and second blades are rotatable about the pivot axis, wherein the first securing device provides a first latching feature arranged to engage a first projected shoulder provided on the first blade holder, and the second securing device provides a second latching feature arranged to engage a second projected shoulder provided on the second blade holder, wherein each securing device comprises a leaf spring received within a recess defined in a shank of a laterally adjacent blade of the first and second blades, and each latching feature is spring biased to naturally project laterally outward from the shank and away from the recess to engage a corresponding one of the first and second projected shoulders, and wherein disengaging the first and second securing devices from the first and second blade holders allows the first and second blades to be separated from the first and second blade holders.

* * * * *